(12) United States Patent
Seel et al.

(10) Patent No.: US 7,262,910 B2
(45) Date of Patent: Aug. 28, 2007

(54) ILLUMINATING DEVICE AND OPTICAL OBJECT-ANALYZING DEVICE

(75) Inventors: Matthias Seel, Munich (DE); Klaus Schaller, deceased, late of Hechendorf (DE); by Ines Schaller, legal representative, Hechendorf (DE)

(73) Assignee: Olympus Biosystems GmbH, Planegg (DE)

( * ) Notice: Subject to any disclaimer, the term of this patent is extended or adjusted under 35 U.S.C. 154(b) by 71 days.

(21) Appl. No.: 10/520,954

(22) PCT Filed: Jul. 10, 2003

(86) PCT No.: PCT/EP03/07513

§ 371 (c)(1),
(2), (4) Date: Sep. 27, 2005

(87) PCT Pub. No.: WO2004/008115

PCT Pub. Date: Jan. 22, 2004

(65) Prior Publication Data

US 2006/0028718 A1    Feb. 9, 2006

(30) Foreign Application Priority Data

Jul. 12, 2002 (DE) .............................. 102 31 667

(51) Int. Cl.
*G02B 21/06* (2006.01)
(52) U.S. Cl. ..................................... 359/388; 359/368
(58) Field of Classification Search ................ 359/368, 359/385, 388
See application file for complete search history.

(56) References Cited

U.S. PATENT DOCUMENTS

| | | | |
|---|---|---|---|
| 3,666,362 A * | 5/1972 | Chance ........................ 356/320 |
| 3,897,154 A * | 7/1975 | Hawes ........................ 356/51 |
| 3,907,430 A | 9/1975 | Mann ......................... 356/100 |
| 4,575,243 A | 3/1986 | Witte ......................... 356/333 |
| 4,660,975 A | 4/1987 | Aughton ..................... 356/308 |
| 4,795,256 A * | 1/1989 | Krause et al. .............. 356/320 |

(Continued)

FOREIGN PATENT DOCUMENTS

DE        36 04 815 A1    8/1987

(Continued)

*Primary Examiner*—Mark A. Robinson
(74) *Attorney, Agent, or Firm*—Morris Manning & Martin LLP; Tim Tingkang Xia, Esq.

(57) ABSTRACT

An illuminating device (10). In one embodiment, the illuminating device includes a light source (12), optical components (16, 18, 20) that define a plurality of light paths (14) originating from the light source, a light-conditioning array (22) on at least one of the plurality of light paths, at least one light output (34) to which an associated device that is to be supplied with light or conditioned light is connectable, at least one light path-selecting unit (24) which is provided with several input light path sections associated with another light path and at least one output light path section leading to said light output or another associated light output. Each light path is optionally connected to the light output via the output light path section or to a predefined or selected light output via a predefined or selected output light path section as a selected light path in a corresponding selection mode of the light path-selecting unit by means of the light path-selecting unit that can be switched between several selection modes.

44 Claims, 5 Drawing Sheets

U.S. PATENT DOCUMENTS

| | | | | |
|---|---|---|---|---|
| 4,843,242 | A | * 6/1989 | Doyle | 250/330 |
| 5,285,254 | A | 2/1994 | De Sa | 356/308 |
| 5,469,255 | A | 11/1995 | Kamada et al. | 356/300 |
| 6,167,173 | A | 12/2000 | Schoeppe et al. | 385/33 |
| 6,486,458 | B1 | 11/2002 | Schoeppe et al. | 250/205 |
| 6,563,632 | B1 | 5/2003 | Schoeppe et al. | 359/368 |
| 6,631,226 | B1 | 10/2003 | Schoeppe et al. | 385/33 |
| 6,686,583 | B2 | 2/2004 | Engelhardt | 250/216 |
| 2002/0003204 | A1 | 1/2002 | Engelhardt | 250/216 |

FOREIGN PATENT DOCUMENTS

| | | |
|---|---|---|
| DE | 42 28 366 A1 | 3/1994 |
| DE | 41 15 401 C2 | 4/1994 |

* cited by examiner

ILLUMINATING DEVICE AND OPTICAL OBJECT-ANALYZING DEVICE

FIELD OF THE INVENTION

The invention relates in one aspect to an illuminator, preferably for microscopic and/or fluorescence-based applications.

BACKGROUND OF THE INVENTION

A fluorescence measuring device comprising an illuminator is known from DE 41 15 401 C2. The illuminator of the fluorescence measuring device comprises two illuminating units each comprising a light source, of which at least one unit is pulsed, and a diffraction grating, which is illuminated by the two illuminating units in such a way in its entrance slit plane that the two beam paths originating from the illuminating units are combined in its exit slit plane and emerge therefrom in one beam path, forming a bichromatic intensity-time profile of varying wavelength. The known fluorescence measuring device serves, according to the details in the patent specification, to determine the ion concentration of an object under investigation, which has been coloured with a fluorescent dye, whose excitation maximum varies as a function of the ion concentration to be determined. By means of an imaging system, the beam path with the bichromatic intensity-time profile is directed on the object under investigation. A detector unit is provided for converting the fluorescent light output by the object under investigation into a measurement signal. The two illuminating units are distinguished in that they each comprise a light guide, whose entrance aperture is exposed via an imaging system to light from the light source assigned thereto and whose exit aperture lies in the entrance slit plane of the diffraction grating. The exit apertures of the light guides are displaceable relative to one another and to the diffraction grating for adjustment of the wavelengths of the light with the bichromatic intensity-time profile impinging on the object under investigation. As far as the structure of the illuminating units is concerned, it is proposed that these comprise two flash lamps as light sources. It is also proposed that the two pulsed illuminating units each comprise a continuous light source and an controllable shutter arranged in the beam path between said light source and the diffraction grating. It is further proposed that the two pulsed illuminating units comprise a common, continuous light source and two separately controllable shutters arranged in the beam path between said light source and the diffraction grating.

A further fluorescence measuring device is known from DE 42 28 366 C2 for determining ion concentrations of an object under investigation dyed with fluorescent dye altering the absorption or fluorescence characteristics as a function of the ion concentration. The fluorescence measuring device comprises an illuminator, a detector unit for receiving the fluorescent light and an evaluator. The illuminator comprises a polychromatic light source and means for selecting predeterminable wavelengths at short time intervals for fluorescent excitation or for simultaneous fluorescent excitation of the object under investigation with any desired predeterminable exposure time for each wavelength and any desired predeterminable dark periods. As means of selecting the predeterminable wavelengths, a holographic volume grating is provided, which is arranged on an adjustable scanner, which may be adjusted into the appropriate wavelength position for generating the wavelengths and setting the exposure time and into a wavelength position which does not excite the system for setting the dark periods. It is proposed to operate the volume grating as a reflection grating.

Further known devices, which may in principle be used as illuminator or as part of an illuminator, are known from U.S. Pat. No. 5,285,254, which describes a monochromator, U.S. Pat. No. 3,907,430, which describes an optical bandpass filter, and U.S. Pat. No. 4,575,243, which describes a monochromator. Reference is further made to U.S. Pat. No. 4,660,975.

SUMMARY OF THE INVENTION

It is an object of the invention to provide an illuminator which allows controlled illumination for instance of an object under investigation with illumination light, wherein at least one parameter of the light or at least one property of the light may be varied in controlled manner, the idea being for example illumination with different wavelengths and/or different intensities.

To achieve this object, an illuminator is provided which comprises:
  a light source;
  optical components, which define a plurality of light paths originating from the light source;
  a light conditioning arrangement in at least one of the light paths,
  at least one light output, to which an associated device to be supplied with light or conditioned light, for example a microscope or a fluorescence measuring device, is connected or may be connected;
  at least one light path selector unit, which comprises a plurality of input light path portions assigned in each case to a different one of the light paths and at least one output light path portion leading to the light output or to an assigned one of the light outputs, wherein, by means of the light path selector unit adjustable between a plurality of selector states, when the light path selector unit is in an appropriate selector state, each of the light paths may selectively be connected as selected light path via the output light path portion to the light output or via a predetermined or selected output light path portion to a predetermined or selected light output.

According to the proposal of the invention, control of the illumination takes place on the basis of a plurality of light paths, of which at least one comprises a light conditioning arrangement. The light conditioning arrangement may for example condition the light incident in the light path with regard to central wavelength and/or spectral bandwidth and/or total photon flux (intensity). By selecting a light path by means of the light path selector unit, the correspondingly conditioned or unconditioned light, which is incident from this light path, is connected to the light output or a predetermined or selected one of a plurality of light outputs and thus provided for illumination. Controlled variation of the light provided at the output, for instance with regard to at least one of the above-mentioned parameters and properties, may take place by changeover to a different, then selected light path. Since this light path provides correspondingly conditioned, in particular differently conditioned, light or unconditioned light from the start and has only to be connected to the light output, short control times are possible for changing-over of the illumination light, which are namely purely switching times for the switching between the light paths.

Such an illumination device has many different uses, for instance for illuminating in microscope-assisted processes, in particular for exciting fluorescent molecules in biological objects under investigation. If two or more outputs are present, a particularly large number of different applications are possible.

A possible application in the field of fluorescence-based investigative procedures is in particular investigations or measuring procedures relating to biological cells. It is of interest, for example, to record the spatial distribution of ions (magnesium, potassium and chloride, but in particular calcium) important for the cell metabolism of a living cell. Dyes (fluorescent indicators) exist which do not impair cell function but which modify their fluorescence behaviour as a function of intracellular ion concentrations. In order to be able to draw conclusions about ion concentration irrespective of the concentration of dye in the dyed cell and the cell thickness, a ratio-metric measurement may be performed, in which fluorescence is determined at two different excitation wavelengths.

Other particular applications are those connected with the GFP method (Green Fluorescent Protein method) and variations thereof, said method being based on the excitation of dyes produced by biological cells themselves.

Another worthwhile approach is to excite with UV light (for example at approximately 360 nm) for a short time during measurement and thus to trigger photolysis of a so-called "caged compound". Using such compounds, ions (e.g. calcium) or cellularly active substances (for instance ATP or cyclic nucleotides) may for example be specifically released by means of UV light exposure, for example in order specifically and optionally intermittently to excite intracellular regulatory processes or to open cell channels. The illuminator according to the invention may advantageously be designed to perform such measurements and investigations or light excitation.

The illuminator according to the invention makes it possible to perform illumination-based measurements particularly quickly and flexibly, e.g. to illuminate an object under investigation at a plurality of wavelengths and different intensities, optionally with a predetermined, defined time interval, for example by introducing the illumination light into a microscope.

The light source preferably is a broadband, continuously operating or pulsed light source. As broadband light source for example a discharge lamp may be provided, for example a xenon lamp. The photon stream emitted by the light source is collected per light path via a suitable optical arrangement available to the person skilled in the art (for example reflector and collecting optics) and transmitted as a light beam into the light path, for example via an individual slit or a corresponding aperture. A light source may be used which emits over a large solid angle. It is then preferable for photon fluxes from the light source travelling in different directions or solid angles each to be separately collected. Light conditioning then takes place in the individual light paths in accordance with the desired illumination, depending on the application.

The light path selector unit may preferably be adjusted into at least one selector state in which no light path is selected, such that none of the light paths is connected with the or with a light output. This configuration of the illuminator provides the possibility of providing defined dark periods in the illumination.

A preferred development of the light path selector unit according to the invention is distinguished in that it comprises at least one optical light deflector element adjustable between a plurality of selection positions. In this context, it is proposed that each selector state may be achieved on the basis of at least one selection position of the light deflector element, light which is incident via the assigned selected light path being diverted in the respective selector state into the output light path portion or into the predetermined or selected output light path portion and light which is incident via the or a respective non-selected light path not being diverted into the or into any output light path portion.

The light path selector unit may comprise at least one mirror arranged to be swivellable or rotatable by means of an actuator. The mirror is adjustable by means of the actuator into different swivelled or rotated positions, which in each case define an angle range or solid angle range over which the mirror receives photons of an in each case assigned light path and diverts them in defined manner into the output light path portion or the predetermined or selected output light path portion and so directs them to the light output or the predetermined or selected light output. The actuator preferably takes the form of a galvanometer in order to enable short switching or control times.

Versatility is obtained if the light path selector unit comprises at least one micromechanical adjusting mirror arrangement with a plurality of micromechanical adjusting mirrors. Intended micromechanical adjusting mirror arrangements are those which may be controlled electrically in order to adjust the adjusting mirrors or selected ones of the adjusting mirrors between a plurality of selection positions. Corresponding semiconductor chips have been introduced onto the market by Texas Instruments, so creating the foundations for "DMD/DLP" (Digital Light Processing) technology. An individual semiconductor chip comprises, for example, hundreds of thousands of microscopically small mirrors which are electrically movable. By means of an assigned electronic control unit, light reflected by the mirror arrangement may be directed for each individual mirror (pixel) either into an optical system or "away" in order, for instance, (in conventional applications) to project an image input into the electronic control unit. In the context of the proposal of the invention, a micromechanical adjusting mirror arrangement of the mentioned type may be adjusted in such a way that different angle of incidence ranges, in particular solid angle of incidence ranges, which are in each case assigned to a light path, are selected and the light incident thereover from the light path is diverted in defined manner into the output light path portion or a predetermined or selected one of a plurality of output light path portions. In this context, the intensity of the forwarded light may be controlled for example in that the number of adjusting mirrors involved in diverting said light is varied in controlled manner or these may be changed over between different positions with a selected pulse duty factor. It should be noted that the adjusting mirrors may take the form of swivel mirrors.

As is already clear from the previous statements, the light conditioning arrangement may comprise an optical wavelength selection arrangement, by means of which at least one predetermined or settable selection wavelength, preferably precisely one predetermined or settable selection wavelength, may be selected with a predetermined or settable selection bandwidth for propagation in the direction of the light path selector unit. A particular option is for a light conditioning arrangement comprising a respective wavelength selection arrangement to be provided in each of the light paths, by means of which light conditioning arrangement selection wavelengths differing with regard to light path may be selected for propagation in the direction of the light path selector unit.

The (respective) wavelength selection arrangement may comprise for example a suitable light filter or a monochromator arrangement (for example a Czerny-Turner grating monochromator).

In addition, the (respective) light conditioning arrangement may comprise an optical polariser arrangement, in order to provide selection with regard to polarisation.

In addition, the light conditioning arrangement may comprise an adjustable optical intensity attenuating arrangement or beam shading arrangement, in order to be able to set an output intensity at the (respective) light output. Intensity may be controlled for example on the basis of conventional neutral filters or adjustable diaphragms. A rotatable shading unit is feasible, for example, which comprises ranges of different degrees of optical density or transmission. Depending on the position of the shading unit, the light beam passing therethrough is shaded to a greater or lesser degree, such that a correspondingly increased or reduced intensity is provided at the output. A homogenising device may be provided, in order to ensure homogeneous illumination despite partial shading of the respective beam. Such homogenisation may be performed by a light guide connected downstream, wherein a light guide provided anyway according to a preferred development is particularly feasible, which guides the illumination light to an assigned optical device, for instance a microscope. The individual areas of the shading unit may be designed as discrete areas or as areas varying continuously in the manner of a graduated filter. The latter makes it possible to control/regulate the intensity continuously.

To control/regulate the intensity of the illumination light, reference should also be made to the fact that this may also be effected by means of the light path selector unit, as already explained with reference to the micromechanical adjusting mirror arrangement. In the case of different light path selector units too, for example in the case of a swivellably or rotatably arranged mirror, the intensity may be correspondingly influenced, for example by focusing the light incident from a light path wholly or partially onto a diaphragm or diverting it completely into the relevant output light path portion.

Advantageously, at least one light trap assigned to the light path selector unit may be provided, to which light trap a non-selected light path may be connected via the light path selector unit. In this way, a very low background intensity may be achieved for the "switched-off status" of the illuminator, which is important for example for fluorescence microscopic applications. Another possibility is to provide a rapid optical shutter (in generally an optical shutter arrangement) in at least one of the light paths or light path portions.

A convenient embodiment of the illuminator is distinguished in that precisely one light output is provided, to which precisely one selected one of the light paths may preferably be connected by means of the light path selector unit.

Versatility is obtained, for example in relation to fluorescence microscopic investigations, if at least two light outputs are provided. To this end, it is proposed in particular that at least two selected light paths may be simultaneously connected to a respective one of the light outputs by means of the light path selector unit or by means of at least two separate light path selector units.

Provision may be made for at least two light path selector units to be adjustable into mutually assigned selector states, in such a way that a selected one of the light paths is connected via these light path selector units to the light output or a predetermined or selected light output.

Particularly preferably, more than two, for example at least three light paths are provided, for example in order to keep more than two (preferably at least three) different illumination wavelengths ready for selection.

To define the light paths, the widest possible range of optical components may be used, in particular reflective components and/or refractive components and/or diffractive components, mirrors and/or lenses and/or diaphragms being particularly feasible. It may reasonably be proposed that the light paths take the form, between the light source and the light path selector unit, at least in part of light guides (for instance optical fibres or optical fibre bundles). On the other hand, however, it is preferable for the light paths to take the form, at least between the light source and the light path selector unit, of free radiation light paths which are not bound to a medium which defines the light path.

For ease of handling and of connection of the illuminator to an associated optical device, it is generally preferable for the light output or the light outputs to be formed on the basis of a (respective) light guide.

The illuminator preferably comprises a control unit controlling the at least one light path selector unit and optionally the light conditioning arrangement or light conditioning arrangements.

The control unit is preferably designed to provide defined adjustment times for adjusting the light path selector unit between its selector states, the idea being, for example for a change from one light path to the other to be performed or performable in approximately 0.1 to 2 ms or even more quickly. Such changeover times may be readily achieved on the basis of for instance a galvanometer as actuator or on the basis of the micromechanical adjusting mirror arrangement. The illuminator thus becomes suitable, for example, for applications in biological microscopy, in which a plurality of different wavelengths, for example two different wavelengths, need to be coupled into a microscope very quickly one after the other (in a few ms). In the case of the mirror which may be swivelled or rotated by means of a galvanometer, the associated optical system will be so designed in this context that the mirror may be of comparatively small construction and accordingly only a small moment of inertia has to be overcome with correspondingly short adjustment times.

Highly complex measurements or investigations may be performed reliably and repeatably when the control unit is designed to adjust the light path selector unit in accordance with at least one predetermined or predeterminable selection program between its selector states.

The invention further relates to an optical object investigation device, comprising an object area, in which an object to be investigated may be placed, an observation beam path, which leads from the object area to an image area, and at least one illumination beam path connected to a light input, by means of which illumination beam path the object area may be illuminated. It is proposed for this object investigation device that it comprises an illuminator according to the invention as described above, which is or may be connected to the light input with a light output.

Although here on the one hand a light input of the object investigation device and on the other hand a light output of the illuminator are mentioned, it is not absolutely essential for one input and one output to be clearly identifiable, but rather they make take the form of an "interchange point" (for example slit or aperture) identifiable as both input and output or of a respective end of a connecting light guide.

The object investigation device may comprise at least one incident-light illumination beam path, preferably at least two incident-light illumination beam paths. The or the respective incident-light illumination beam path may coincide at least in part with the observation beam path. In addition, the object investigation device may comprise at least one transmitted-light illumination beam path.

A preferred development of the object investigation device is distinguished in that it comprises at least two, preferably at least three illumination beam paths, which may be supplied alternately or—preferably—simultaneously with illumination light from the illuminator.

The object investigation device may comprise a microscope, which comprises the object area, the observation beam path and the at least one illumination beam path. Another option is for the object investigation device to comprise a fluorescence measuring device, which comprises the object area, the observation beam path and the at least one illumination beam path and optionally the microscope mentioned. The object investigation device may be identifiable overall as a fluorescence measuring device or a microscope.

BRIEF DESCRIPTION OF THE DRAWINGS

The invention is explained in more detail below with reference to exemplary embodiments illustrated in the Figures.

DETAILED DESCRIPTION OF THE INVENTION

Figure 1:
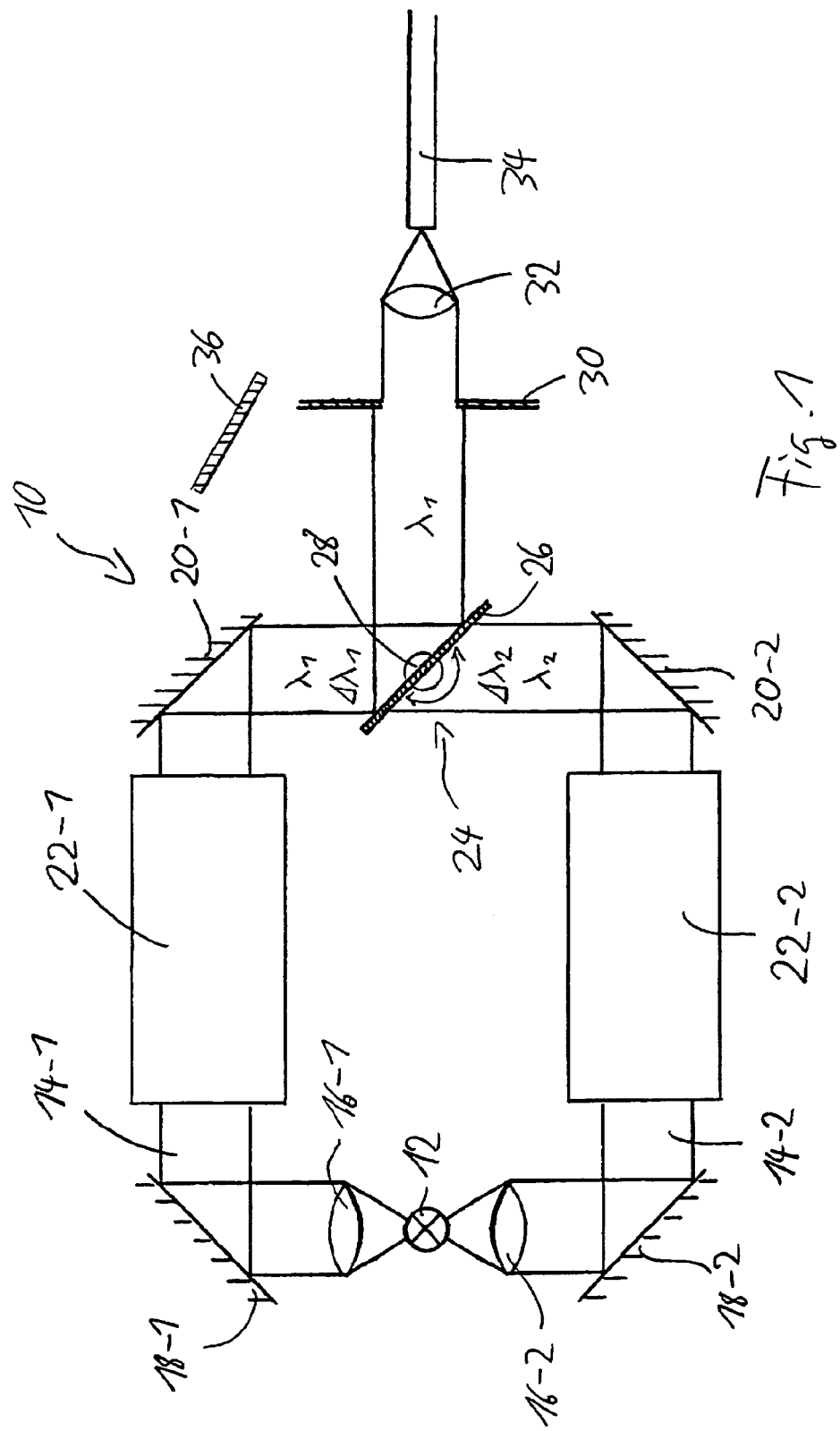
FIG. 1 shows a first exemplary embodiment of an illuminator according to the invention, which comprises two light paths selectable by means of a light path selector unit, in each of which light paths a light conditioning arrangement is arranged, and a light output.

FIG. 1 shows a first example of an illuminator 10 according to the invention, which comprises two light paths 14-1 and 14-2 originating from a common light source 12. To define the light paths, there is provided a respective lens arrangement 16-1 or 16-2 respectively (in each case comprising at least one lens) and two deflecting mirrors 18-1, 20-1 and 18-2, 20-2 respectively. In the exemplary embodiment, the deflecting mirrors are arranged relative to the lamp 12 and relative to one another in such a way that the deflecting mirrors in each case divert the light paths by approximately 90° and the light paths 14-1 and 14-2 are substantially parallel to one another in places. Such an arrangement is not compulsory, however.

In the two light paths 14-1 and 14-2, here in particular in a respective light path portion extending between the deflecting mirrors 18-1 and 20-1 or 18-2 and 20-2 respectively, there is in each case contained a light conditioning arrangement 22-1 or 22-2 respectively, which conditions the light incident from the lamp or light source 12 with regard to at least one parameter or one light property, for example wavelength selection. In the exemplary embodiment shown, wavelength selection is performed, and the light conditioning arrangement 22-1 embodied as a wavelength selection arrangement or comprising a wavelength selection arrangement allows through light at a central wavelength $\lambda_1$ with a passband width $\Delta\lambda_1$. The same applies to the light conditioning arrangement 22-2 constructed as a wavelength selection arrangement or comprising a wavelength selection arrangement, which allows light through at a central wavelength $\lambda_2$ with a passband width of $\Delta\lambda_2$. The central wavelengths $\lambda_1$ and $\lambda_2$ may lie comparatively far apart or comparatively close together, for example they may be only 20 nm apart. The wavelength selection arrangements may be so configured that the light allowed through is very narrowband, for example in order specifically to excite special atomic or molecular transitions.

A broadband discharge lamp, for example a xenon lamp, may be used as the light source for example.

The light conditioning arrangements may advantageously also contain further light-influencing or conditioning elements, for example polarisers for providing polarised light, neutral filters or generally intensity attenuators or beam shaders for controlling the amount of photons allowed through and thus the intensity. Consideration is given, for example, to the use of a beam shading arrangement corresponding to the example of FIG. 6.

The wavelength selection arrangements may for example take the form of a suitable spectral filter or a monochromator arrangement. The selected wavelength and ideally also the passband width are preferably adjustable. A Czerny-Turner grating monochromator may for example find use as a wavelength selection arrangement.

The deflecting mirrors 20-1 and 20-2 direct the light leaving the respective light conditioning arrangement 22-1 or 22-2 in the direction of a light path selector unit 24, which, in the exemplary embodiment of FIG. 1, takes the form of a rotatably mounted mirror 26 and an associated actuator 28 and may be controlled by means of an associated control electronic unit. The actuator 28 preferably takes the form of a galvanometer, so as to be able to adjust the mirror between different selected rotary positions with short adjustment times. To this end, the mirror 26 and all the rest of the optical system of the illuminator are preferably so configured relative to one another that a mirror with a comparatively small reflective surface and consequently low inertia mass may be used. Another option is to use a linear actuator, which acts for example via a gearing on a rotary mirror or on a linearly displaceable mirror arrangement.

In a selection position shown in FIG. 1, the deflecting mirror 26 of the light path selector unit 24 diverts the light incident from the deflecting mirror 20-1 by approximately 90° in the direction of a diaphragm 30 and a coupling optical system 32 arranged downstream of the diaphragm, which coupling optical system 32 couples the light incident into the coupling optical system 32 as efficiently as possible into a light guide 34, e.g. an optical fibre, forming the single light output of the illuminator. The optical fibre 34 (or generally a light guide or a light guide bundle 34) accordingly guides light with the central wavelength $\lambda_1$ and the spectral bandwidth $\Delta\lambda_1$.

In a further selection position, for instance corresponding to rotation of the mirror 26 by 90° relative to the illustration in FIG. 1, the latter diverts the light incident from the deflecting mirror 20-2 with the wavelength $\lambda_2$ and the bandwidth $\Delta\lambda_2$ in the direction of the diaphragm 30 and the coupling optical system 32, in order to couple this light into the light guide 34. In the two selection positions, each corresponding to selection of the light path 14-1 or 14-2, the light irradiated from the in each case other light path falls on the back of the galvanometer mirror 26 preferably embodied as a light trap. In at least one further selected rotated position of the galvanometer mirror 26, the light incident from the one light path onto the mirror falls onto or into a light trap 36 and the light incident from the other light path falls onto the non-reflecting back, which is preferably light-absorbing or embodied as a light trap, of the galvanometer mirror 26. In this selection position of the galvanometer mirror 26, no illumination light is coupled into the optical fibre 34, and the light traps ensure low background intensity in this state. Corresponding effects may also be achieved by means of at least one shutter arrangement at a suitable point in the illuminator 10, which should be correspondingly quickly actuatable with regard to desired switching times.

The light path selector unit may also be constructed on the basis of other components available to the person skilled in the art. Micro-electromechanical systems are feasible, for example, which comprise an electrically adjustable adjusting mirror arrangement (c.f. DMD/DLP technology).

It should be noted that the light path selector unit may also be used, irrespective of its structure, for intensity control of the light provided via the light guide 34, by diverting the particular light beam in part, with a controlled fraction, onto the diaphragm 30, such that correspondingly fewer photons enter the light guide 34 per unit time. There is no fear of the light exiting from the light guide at the other end exhibiting non-uniformities, since the light guide ensures homogenisation.

By means of the illuminator according to the invention, light with parameters preselected for the individual light path may be made available to the coupling optical system 32 via both light paths in a selected time sequence and thus to a connected optical device via the light guide 34. A very quick change should be possible from one light path to the other, for example within 0.2 to 2 ms, in order to couple different wavelengths very quickly one after the other (at intervals of a few ms) into a corresponding optical device, in particular a microscope, for example for biological applications, in particular biological microscopy.

Apart from the output light guide 34, the light paths are embodied as "free radiation light paths", i.e. are not formed of light guides. This makes it possible to collect the light emitted by the light source 12 over large solid angle ranges for both light paths and avoids losses on coupling into the light guide.

Figure 2:
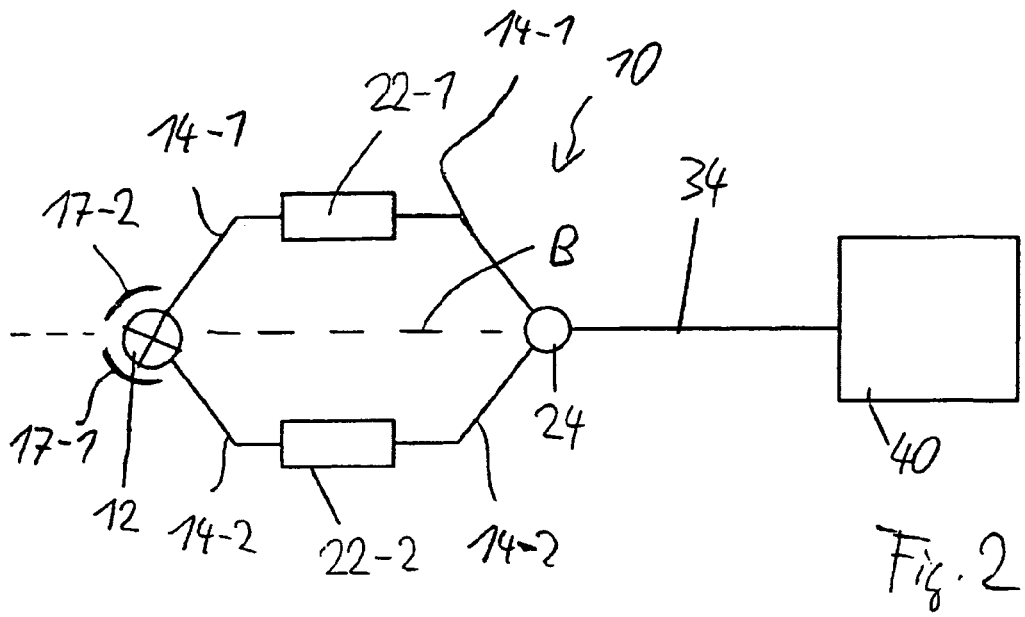
FIG. 2 shows an illuminator, corresponding in configuration substantially to the exemplary embodiment of FIG. 1, combined with a microscope, wherein the illuminator and the microscope may be identified as an example of an optical object investigation device according to the invention.

FIG. 2 is a schematic representation of an illuminator 10 with two light paths, which may correspond in their configuration substantially to the exemplary embodiment of FIG. 1. The two light paths 14-1 and 14-2 originate from the light source 12 and are guided through the light conditioning arrangements 22-1 and 22-2 respectively, which optionally take the form of "light selectors". A light path selector unit 24 represented merely by a circle selects a selected one of the two light paths for connection to the output conductor 34 serving as a light output, which conductor 34 supplies corresponding light to an optical device, here a microscope 40.

FIG. 2 also shows schematically reflectors 17-1 and 17-2 assigned to the light paths 14-1 and 14-2 originating from the light source 12 with their respective optical axes at an angle of less than 90° relative to a reference axis B, which reflectors reflect light from the light source 12 falling into a respective solid angle range, which is opposite to the incident solid angle range of the respective light path, into the relevant incident solid angle range, in order to collect the light originating from the light source 12 per light path over a correspondingly enlarged solid angle.

Further exemplary embodiments of advantageous illuminators are explained below with reference to FIGS. 3 to 5, wherein identical reference numerals are used for similar or matching components, which numerals may differ from the previously used reference numerals only by a count digit appended after a hyphen.

Figure 3:
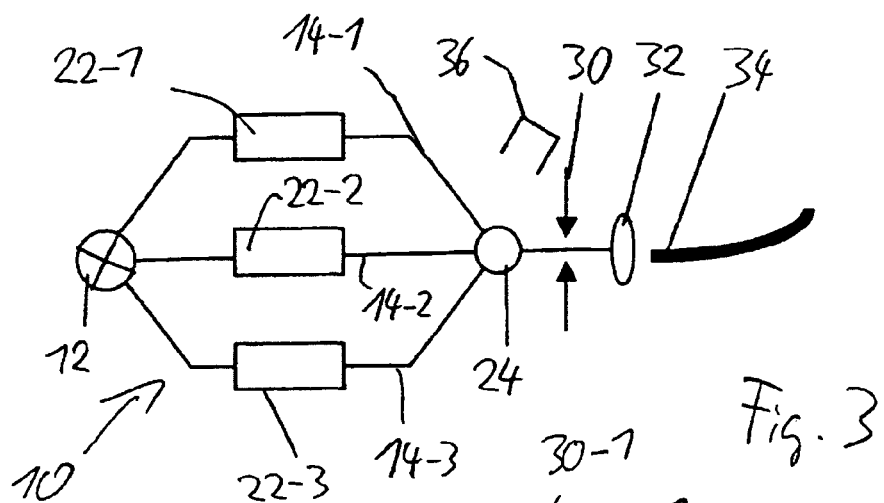
FIG. 3 shows a further example of an illuminator according to the invention, comprising three light paths and one light output, wherein any desired one of the light paths may be connected to the light output by means of a light path selector unit.

FIG. 3 shows an advantageous embodiment with three light paths 14-1, 14-2 and 14-3, which in each case lead through a light conditioning arrangement 22-1 or 22-2 or 22-3 respectively. Each of the light paths may be selected for coupling of the incident light into the light guide 34 by means of the light path selector unit 24. At any one time, only one light path may be selected for this purpose.

Figure 4:
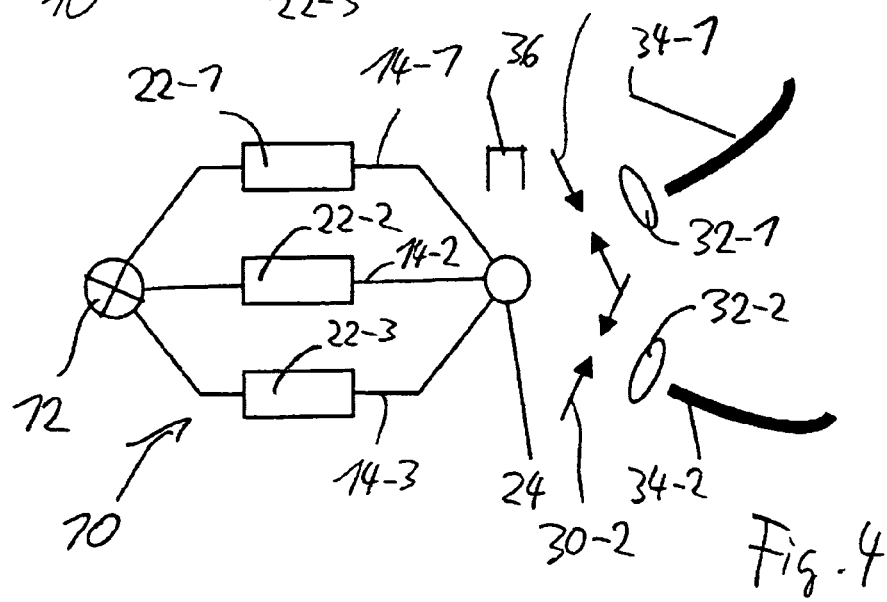
FIG. 4 shows an example of an illuminator according to the invention with two light paths and two light outputs, wherein any desired one of the light paths may be connected to a selected one of the light outputs, but at any one time only one light output, as selected output, can receive light from one of the light paths.

The exemplary embodiment of FIG. 4 differs from the exemplary embodiment of FIG. 3 in that two light guides 34-1 and 34-2 in each case serving as light outputs are provided, to each of which there is respectively assigned one coupling optical system 32-1 or 32-2 and one diaphragm 30-1 or 30-2 arranged upstream thereof. The two light outputs 34-1 and 34-2 may be supplied with light from any one of the light paths 14-1, 14-2 and 14-3 by adjusting the light path selector unit 24 into corresponding selection positions or—more generally—selector states. At any one time, only one of the light outputs may in each case be supplied with illumination light.

Figure 5:
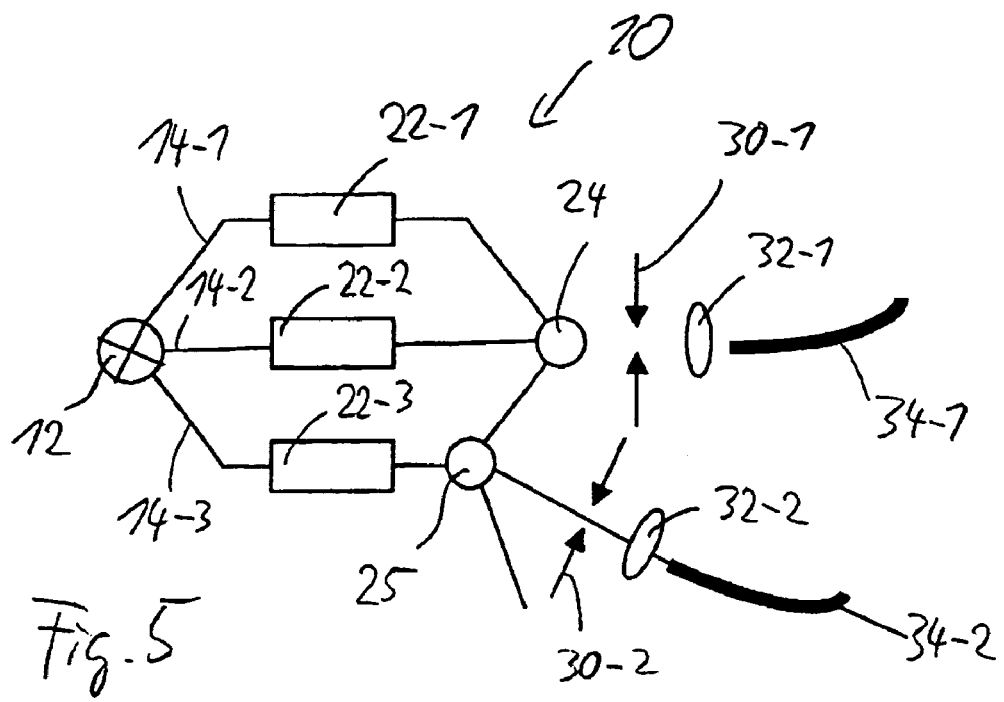
FIG. 5 shows an exemplary embodiment of an illuminator according to the invention with three light paths and two light outputs, in which, on the basis of two light path selector units, both light outputs may simultaneously receive light from an in each case assigned (selected) one of the light paths.

FIG. 5 shows an advantageous illuminator, which likewise comprises three light paths 14-1, 14-2 and 14-3 with a respective light conditioning arrangement 22-1, 22-2 or 22-3. Like the illuminator in FIG. 4, the illuminator in FIG. 5 comprises two light guides 34-1 and 34-2 in each case serving as light outputs, with assigned components 30-1, 30-2, 32-1 and 32-2 which may be served simultaneously with light from a respective light path by means of two light path selector units 24 and 25. According to the configuration shown schematically in FIG. 5, the output 34-1 may be supplied with light from the light path 14-1 or 14-2 while the output 34-2 is simultaneously supplied with light from the light path 14-3. In addition, the light path selector unit 24 may be adjusted into a first and a second state, by diverting the light incident from the light path 14-1 (first state) or the light incident from the light path 14-2 (second state) in the direction of the light path selector unit 25, which, in a corresponding selector state, couples the light irradiated thereon into the output conductor 34-2 via the coupling optical system 32-2. Conversely, it is possible to connect the light path 14-3 to the output light guide 34-1 via the light path selector unit 25 and the light path selector unit 24. In the latter three states of the illuminator, in each case only one of the output light guides is supplied with light from the relevant light path.

Here, a light path selector unit configuration was required, according to which at any one time a selected light path may be connected only with a determined or selected one of the light outputs and according to which a light output may at any one time receive light from only one light path. This is the case, for example, when the light path selector unit comprises an adjustable galvanometer mirror or the like for diversion purposes. Then only alternating supply of two or more light outputs with the light from a selected light path or alternating supply of a light output with light from more than one light path is feasible.

Light path selector unit configurations are also wholly feasible, however, in which a part of the light irradiating from a selected light path is coupled into a first light output and another part of the light irradiating from this light path is coupled into at least one further light output. In addition it is wholly feasible for one light output to receive light simultaneously from a plurality of light paths. For example, in the case of the mentioned micromechanical mirror arrangement it is possible to adjust a proportion of the microscopic adjusting mirrors into a first selection position coupling light from one light path into a first output and at least a further proportion of the micromechanical mirrors into a further selection position coupling the light from the same light path into another output. In addition, light could be supplied by means of corresponding proportions from a plurality of light paths to a jointly assigned light output.

Figure 6:
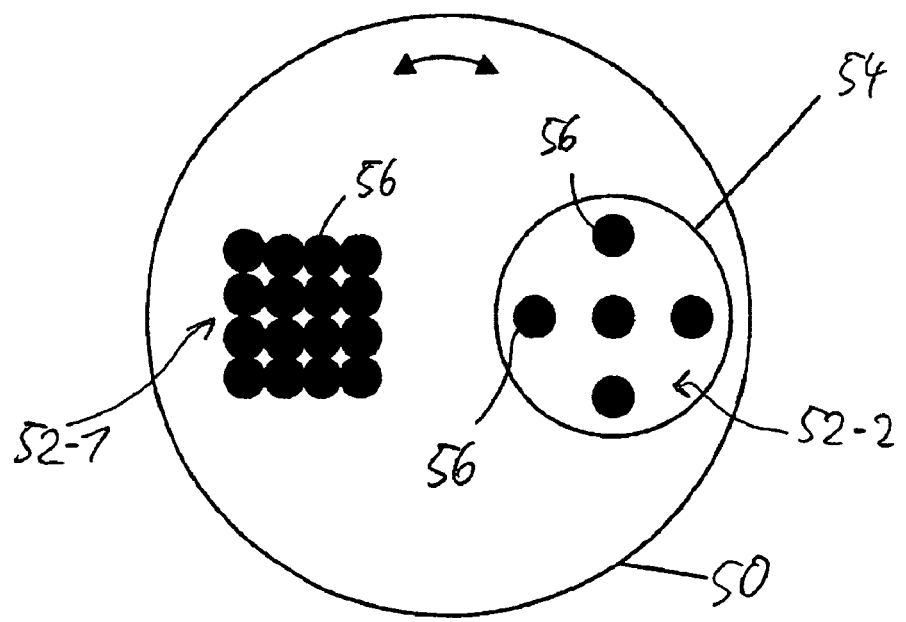
FIG. 6 shows a beam shading arrangement usable as a light conditioning arrangement or part of a light conditioning arrangement on the basis of a rotatable shading wheel.

FIG. 6 shows a shading unit 50 embodied as a rotary disk, which may advantageously be used in a light path as a light conditioning arrangement or part of a light conditioning arrangement. The rotary disk 50 comprises a plurality of fields 52-1 and 52-2, which may be adjusted by rotation of the disk into a light beam, represented by a circle 54, of the respective light path, in order to shade the beam partially and to a greater or lesser extent by opaque or light-impervious zones 56. In the case of a configuration of the illuminator with at least one output light guide, the respective light guide ensures the necessary homogeneity of illumination in the connected optical device. Depending on the position of the disk 50, the intensity provided is reduced in accordance with the shading achieved. The individual zones of the shading unit may be designed discretely (as illustrated in FIG. 6) or in the manner of a graduated filter. The latter makes it possible to control the intensity continuously.

It should be pointed out that it is also perfectly feasible for the illuminator according to the invention to be embodied with more than two light outputs, optionally output light guides.

An advantageous application for an illuminator according to the invention will be explained below with reference to FIG. 7. A microscope arrangement 60 is shown, which is provided for example for fluorescence microscopic applications. Examples of feasible applications are those mentioned in patents DE 41 15 401 C2 and DE 42 28 366 C2.

The microscope arrangement 60 comprises an observation beam path 62, which images an object plane 64 into an image plane 66. Imaging takes place by means of an imaging arrangement comprising at least two lenses or objectives 68 and 70 such as are known per se from the prior art. For measurements or investigations, an object or microscope slide with object 72 may be arranged in the object plane 64. In the image plane 66, a detector arrangement may be arranged, for example a single detector (for instance a semiconductor detector) or—for two-dimensional resolution—a detector field (for instance a CCD chip). A corresponding detector is designated 74 in FIG. 7.

Figure 7:
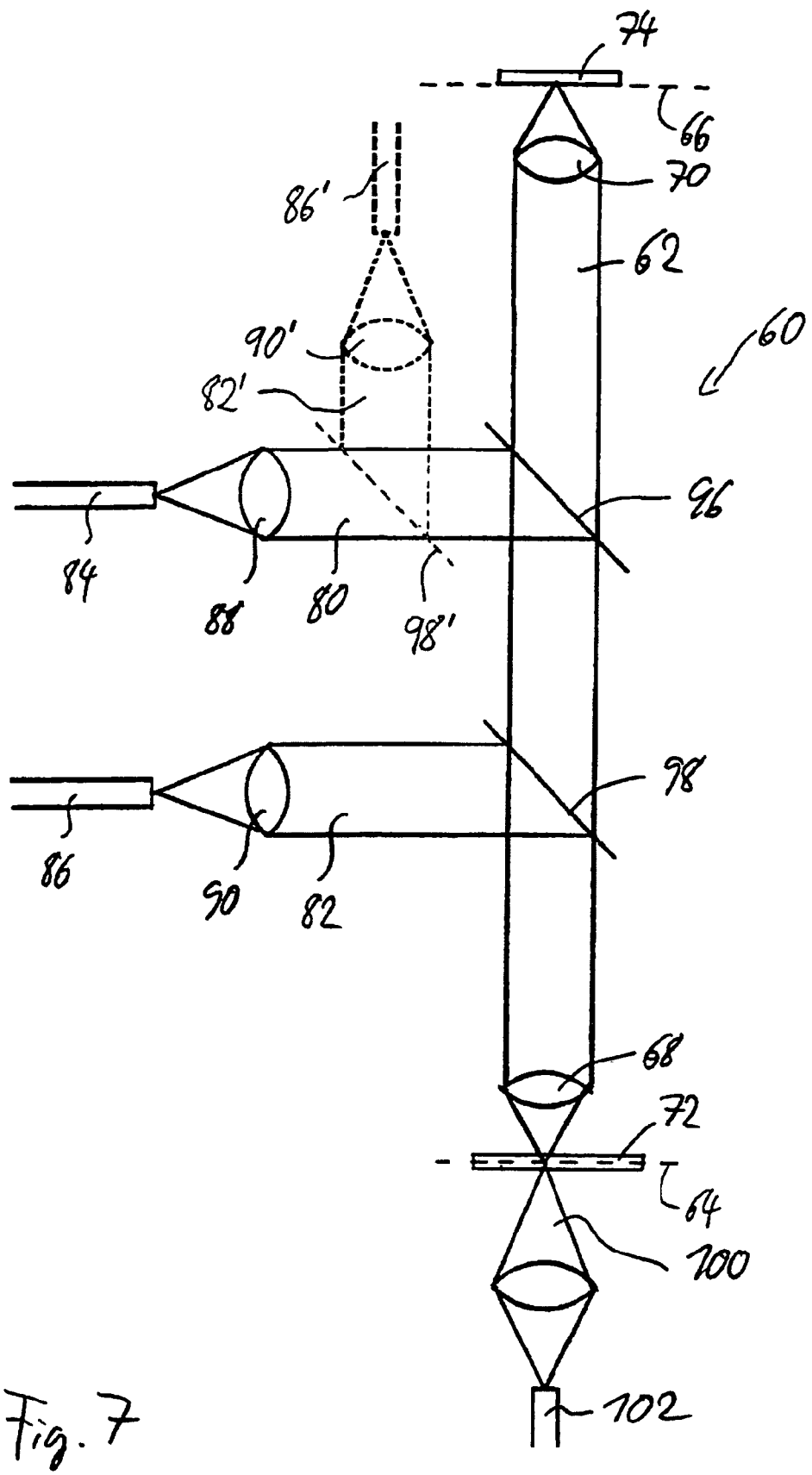
FIG. 7 shows an optical fluorescence microscopy arrangement with two incident-light illumination beam paths and one transmitted-light illumination beam path, to which illumination light may be supplied by an illuminator according to the invention. The illuminator and the fluorescence microscopy arrangement may be regarded in combination as an example of an object investigation device according to the invention.

The microscope arrangement of FIG. 7 comprises two incident-light illumination beam paths 80 and 82, which may be supplied with illumination light from an assigned illuminator via a respective light guide 84 or 86 respectively. The light guides 84 and 86 may for example comprise the light guide 34-1 and the light guide 34-2 of the illuminator according to FIG. 4 or FIG. 5. Another possibility is that either the light guide 84 or the light guide 86 represents the output light guide 34 according to the examples of FIGS. 1 to 3. The light leaving the respective light guide is coupled into the respective illumination beam path by means of a suitable imaging optical system (represented by a lens 88 or 90 respectively), for example in such a way that "critical illumination" is achieved, in which the required visual field is fully and uniformly illuminated with light from the respective light guide. To this end, the outlet end of the respective light guide is imaged into the object plane 34. Other illumination types, e.g. so-called Köhler illumination, may also be achieved.

Provision of the two or at least two incident-light illumination beam paths makes it possible to illuminate the object 72 simultaneously with light exhibiting two different wavelengths. For example, the visual field required may be uniformly and fully illuminated by incident light by means of the beam path 80 (for instance the mentioned "critical illumination"). Light of a different wavelength may additionally be irradiated into the object plane via the beam path 82, for example in order to activate "caged compounds" in the object, such that these release substances stored in the "cage" which, for example, switch channels in biological cells to open. Such caged compounds may be activated specifically by the irradiation of UV light. The UV light required for release of the active substances may be irradiated according to the example mentioned herein via the beam path 82 into the object plane 64, wherein it may be eminently sensible also to provide "critical illumination" of the object plane with the UV light.

Figure 8:
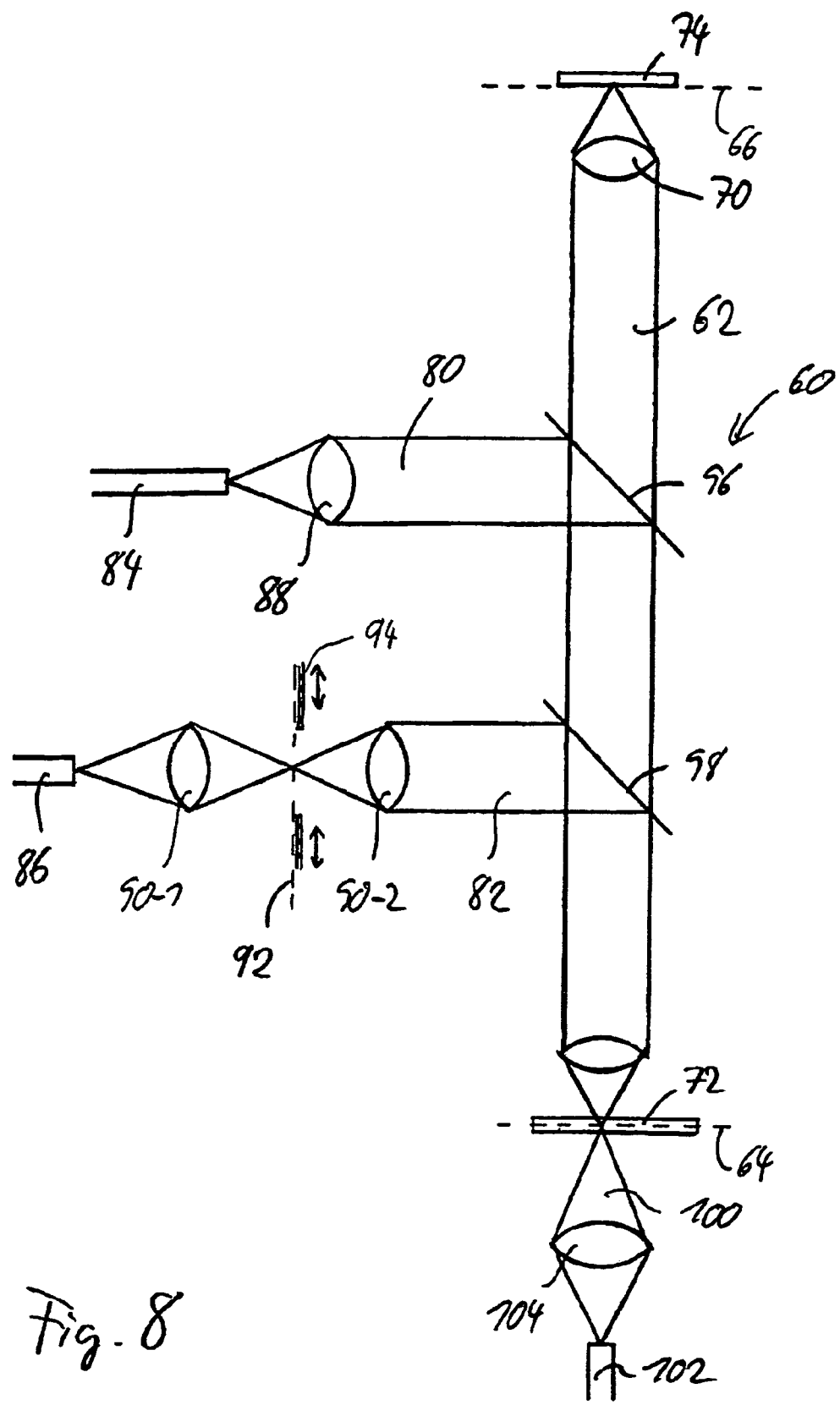
FIG. 8 shows a modification of the fluorescence microscopy arrangement of FIG. 7, in which diaphragms and/or masks may be arranged in an intermediate image plane of the one incident-light illumination beam path, in order to be able to illuminate defined subareas of an object area.

FIG. 8 shows a variant embodiment in which an intermediate image plane 92 is provided in the illumination beam path 82, in which plane masks or patterns may be arranged in order to be able specifically to illuminate particular areas of the object 72 for activation of caged compounds with UV light. For specific illumination of particular areas, an adjustable diaphragm 94 may additionally also be provided in the incident-light illumination beam path 82, more precisely in the intermediate image plane 92 or closely adjacent thereto. The intermediate image plane 92 is formed by an imaging arrangement 90-1 and 90-2, which is represented in FIG. 8 by two lenses.

An image defined in the intermediate image plane 92 by a mask or a pattern may be firmly set relative to the visual field. In this case, it is convenient for the object under investigation 72 to be adjustable relative to the beam path for instance with a microscope stage. Another option is for the respective mask or the respective pattern to be adjustable in the intermediate image plane 92 or for the image of this mask in the object plane to be adjustable optically (for instance by means of a deflecting optical system).

Adaptation of a respective mask to the respective object under investigation may be provided, for example on the basis of an overview recording of the object, for instance in order to define a region in a cell to be investigated in which the cell is to be treated with the released caged compounds. As a result of release of the caged compounds, changes take place in the object, which may be observed directly or indirectly on detection of the fluorescent light originating from the object. Advantageously, a correspondingly two-dimensional image may be displayed on a screen by means of a detector field 74.

The measuring applications mentioned here should be understood to be examples only. Other investigations, e.g. FRAP experiments, may also be performed.

It should be added with reference to the microscope arrangements according to FIGS. 7 and 8 that the two incident-light beam paths 80 and 82 coincide partly with the observation beam path 62. To this end, two dichroic mirrors 96 and 98 are provided, which reflect the illumination wavelengths of the light irradiated from the light guide 84 or 86 into the observation beam path 62, but let through fluorescent light originating from the object 72 in the direction of the image plane 66.

FIG. 7 additionally also shows in broken lines the possibility of bringing together a plurality of incident-light illumination beam paths, namely the incident-light illumination beam paths 80 and 82', prior to reflection into the observation beam path 62 by means of a dichroic mirror 98' and then reflecting them jointly by means of the dichroic mirror 96 into the observation beam path 63. The incident-light beam path 82' (with associated light guide 86' and associated imaging optical system 90') may replace the incident-light beam path 82 in this respect or be provided in addition thereto.

The microscope arrangements 60 of FIGS. 7 and 8 additionally comprise in each case a transmitted-light beam path 100, which may be supplied with illumination light from an illuminator according to the invention by means of a light guide 102. The light guide 102 may for example correspond to one of the output light guides 34 or 34-1 or 34-2 of the exemplary embodiments of FIGS. 1 to 5. The light guide may further also correspond to a third output light guide which is additional with respect to these exemplary embodiments.

Transmitted-light illumination of the object 72 may take place, for example, in such a way that the output end of the light guide 102 is imaged into the object plane 64 by means of a corresponding optical system 104. Other types of illumination known in the specialist field are also suitable.

For example, it is feasible for the transmitted-light illumination beam path 100 to be used in combination with the incident-light illumination beam path 80, in order to be able to switch between "incident-light fluorescence" illumination and a "transmitted-light contrast method" during an investigation, in particular for example especially for recording an image.

The invention claimed is:

1. An optical object investigation device, comprising a microscope having an object area, in which an object to be investigated is to be placed, an observation beam path, which leads from the object area to an image area, and at least one illumination beam path connected to a light input for illuminating the object area, and an illuminator having a light source wherein the illuminator is connectable to the light input with a light output,
characterised in that
  the illuminator comprises optical components, which define a plurality of light paths originating from the light source;
  in at least one of the plurality of light paths a light conditioning arrangement is provided, in order to supply the microscope with conditioned light via the light output;
  the illuminator comprises at least one light path selector unit, which comprises a plurality of input light path portions assigned in each case to a different one of the plurality of light paths and at least one output light path portion leading to the light output or to an assigned one of a plurality of light outputs of the illuminator;
  a control unit controlling the light path selector unit is provided, whereby the light path selector unit is selectively adjustable between a plurality of selector states in such a way that, when the light path selector unit is in an appropriate selector state, each of the plurality of light paths is selectively connected as a selected light path via the output light path portion to the light output or via a predetermined or selected output light path portion to a predetermined or selected light output, in order to supply the microscope with light or conditioned light from the selected light path;
  the control unit is designed to adjust the light path selector unit in a selected time sequence in accordance with a predeterminable selection program in a defined manner between its selector states and to provide defined adjustment times for adjusting the light path selector unit between its selector states; and
  the light path selector unit comprises at least one optical light deflector element adjustable between a plurality of selection positions, wherein each selector state is achieved on the basis of at least one selection position of the at least one optical light deflector element, light which is incident via the assigned selected light path being diverted in the respective selector state into the output light path portion or into the predetermined or selected output light path portion and light which is incident via a respective non-selected light path not being diverted into any output light path portion.

2. The object investigation device according to claim 1, characterised in that the light path selector unit is adjustable to be in at least one selector state in which no light path is selected, such that none of the plurality of light paths is connected to a light output.

3. The object investigation device according to claim 1 or characterised in that the at least one optical light deflector element is arranged to be swivellable or rotatable by means of an actuator.

4. The object investigation device according to claim 3, characterised in that the actuator is formed in the form of a galvanometer.

5. The object investigation device according to claim 1, characterised in that the light path selector unit comprises at least one micromechanical adjusting mirror arrangement with a plurality of micromechanical adjusting mirrors, which is controllable electrically in order to adjust the plurality of micromechanical adjusting mirrors or selected ones of the plurality of micromechanical adjusting mirrors between a plurality of selection positions.

6. The object investigation device according to claim 5, characterised in that the plurality of micromechanical adjusting mirrors are formed in the form of swivel mirrors.

7. The object investigation device according to claim 1, characterised in that the light conditioning arrangement comprises an optical wavelength selection arrangement, whereby at least one predetermined or settable selection wavelength, preferably precisely one predetermined or settable selection wavelength, is selected within a predetermined or settable selection bandwidth for propagation in the direction of the light path selector unit.

8. The object investigation device according to claim 7, characterised in that in each of the plurality of light paths the light conditioning arrangement comprises a respective wavelength selection arrangement, whereby light conditioning arrangement selection wavelengths differing with regard to the light path are selected for propagation in the direction of the light path selector unit.

9. The object investigation device according to claim 1, characterised in that the light conditioning arrangement comprises an optical polariser arrangement.

10. The object investigation device according to claim 1, characterised in that the light conditioning arrangement comprises an adjustable optical intensity attenuating arrangement or beam shading arrangement for setting an output intensity at the light output.

11. The object investigation device according to claim 1, characterised by at least one light trap assigned to the light path selector unit, wherein the at least one light trap is connected to a non-selected light path via the light path selector unit, and/or by an optical shutter arrangement in at least one of the plurality of light paths or light path portions.

12. The object investigation device according to claim 1, characterised in that one light output is provided, wherein the one light output is preferably connected to one selected light path of the plurality of light paths by means of the light path selector unit.

13. The object investigation device according to claim 1, characterised in that at least two light outputs are provided, and at least two selected light paths are simultaneously connected to the at least two light outputs by means of the light path selector unit or by means of at least two light path selector units.

14. The object investigation device according to claim 13, characterised in that the at least two light path selector units are adjusted into mutually assigned selector states, in such a way that a selected light path of the plurality of light paths is connected via these light path selector units to the light output or a predetermined or selected light output.

15. The object investigation device according to claim 1, characterised in that more than two light paths are provided.

16. The object investigation device according to claim 1, characterised in that reflective components and/or refractive components and/or diffractive components are provided as the optical components defining the plurality of light paths.

17. The object investigation device according to claim 1, characterised in that mirrors and/or lenses and/or diaphragms are provided as the optical components defining the plurality of light paths.

18. The object investigation device according to claim 1, characterised in that the plurality of light paths is formed in the form, at least between the light source and the light path selector unit, of free radiation light paths which are not bound to a medium which defines the light path.

19. The object investigation device according to claim 1, characterised in that the light output or the plurality of light outputs are formed on the basis of a light guide.

20. The object investigation device according to claim 1, characterised in that the control unit controls the light conditioning arrangement or light conditioning arrangements.

21. The object investigation device according to claim 1, characterised in that the object investigation device further comprises at least one incident-light illumination beam path, preferably at least two incident-light illumination beam paths, which optionally coincide(s) at least in part with the observation beam path.

22. The object investigation device according to claim 1, characterised in that the object investigation device further comprises at least one transmitted-light illumination beam path.

23. The object investigation device according to claim 1, characterised in that the object investigation device further comprises at least two, preferably at least three illumination beam paths, which are supplied alternately or preferably simultaneously with illumination light from the illuminator.

24. The object investigation device according to claim 1, characterised in that the object investigation device further comprises a fluorescence measuring device comprising the object area, the observation beam path and the at least one illumination beam path and including the microscope.

25. An illuminator for an optical object investigation device, which comprises a microscope having an object area, in which an object to be investigated is to be placed, an observation beam path, which leads from the object area to an image area, and at least one illumination beam path connected to a light input for illuminating the object area comprising:
   a light source;
   a plurality of optical components, which define a plurality of light paths originating from the light source;
   a light conditioning arrangement in at least one of the plurality of light paths,
   at least one light output, to which the microscope to be supplied with light or conditioned light is connectable;
   at least one light path selector unit, which comprises a plurality of input light path portions assigned in each case to a different one of the plurality of light paths and at least one output light path portion leading to a light output or to an assigned one of the at least one light output; and
   a control unit controlling the at least one light path selector unit whereby the light path selector unit is selectively adjustable between a plurality of selector states in such a way that, when the light path selector unit is in an appropriate selector state, each of the plurality of light paths is selectively selected a light path via the output light path portion to the light output or via a predetermined or selected output light path portion to a predetermined or selected light output, in order to supply the microscope with light or conditioned light from the selected light path,
   wherein the control unit is designed to adjust the light path selector unit in a selected time sequence in accordance with a predeterminable selection program in a defined manner between its selector states and to provide defined adjustment times for adjusting the light path selector unit between its selector states; and
   wherein the light path selector unit comprises at least one optical light deflector element adjustable between a plurality of selection positions, wherein each selector state is achieved on the basis of at least one selection position of the at least one optical light deflector element, light which is incident via the assigned selected light path being diverted in the respective selector state into the output light path portion or into the predetermined or selected output light path portion and light which is incident via the or a respective non-selected light path not being diverted into the or into any output light path portion.

26. The illuminator according to claim 25, characterised in that the light path selector unit is adjustable to be in at least one selector state in which no light path is selected, such that none of the plurality of light paths is connected to a light output.

27. The illuminator according to claim 25 characterised in that the at least one optical light deflector element is arranged to be swivellable or rotatable by means of an actuator.

28. The illuminator according to claim 27, characterised in that the actuator is formed in the form of a galvanometer (28).

29. The illuminator according to claim 25, characterised in that the light path selector unit comprises at least one micromechanical adjusting mirror arrangement with a plurality of micromechanical adjusting mirrors, which is controlled electrically in order to adjust the plurality of micromechanical adjusting mirrors or selected ones of the plurality of micromechanical adjusting mirrors between a plurality of selection positions.

30. The illuminator according to claim 29, characterised in that the plurality of micromechanical adjusting mirrors are formed in the form of swivel mirrors.

31. The illuminator according to claim 25, characterised in that the light conditioning arrangement comprises an optical wavelength selection arrangement, whereby at least one predetermined or settable selection wavelength, preferably precisely one predetermined or settable selection wavelength, is selected within a predetermined or settable selection bandwidth for propagation in the direction of the light path selector unit.

32. The illuminator according to claim 31, characterised in that in each of the plurality of light paths (14-1, 14-2; 14-1, 14-2, 14-3) the light conditioning arrangement comprises a respective wavelength selection arrangement, whereby light conditioning arrangement selection wavelengths differing with regard to the light path are selected for propagation in the direction of the light path selector unit.

33. The illuminator according to claim 25, characterised in that the light conditioning arrangement comprises an optical polariser arrangement.

34. The illuminator according to claim 25, characterised in that the light conditioning arrangement comprises an adjustable optical intensity attenuating arrangement or beam shading arrangement for setting an output intensity at the light output.

35. The illuminator according to claim 25, characterised by at least one light trap assigned to the light path selector unit, wherein the at least one light trap is connectable to a non-selected light path via the light path selector unit, and/or by an optical shutter arrangement in at least one of the plurality of light paths or light path portions.

36. The illuminator according to claim 25, characterised in that one light output is provided, wherein the one light output is preferably connected to one selected light path of the plurality of light paths by means of the light path selector unit.

37. The illuminator according to claim 25, characterised in that at least two light outputs are provided, and at least two selected light paths are simultaneously connected to the at least two light outputs by means of the light path selector unit or by means of at least two light path selector units.

38. The illuminator according to claim 25, characterised in that the at least two light path selector units are adjusted into mutually assigned selector states, in such a way that a selected light path of the plurality of light paths is connected via these light path selector units to the light output or a predetermined or selected light output.

39. The illuminator according to claim 25, characterised in that more than two light paths are provided.

40. The illuminator according to claim 25, characterised in that reflective components and/or refractive components and/or diffractive components are provided as the optical components defining the plurality of light paths.

41. The illuminator according to claim 25, characterised in that mirrors and/or lenses and/or diaphragms are provided as the optical components defining the plurality of light paths.

42. The illuminator according to claim 25, characterised in that the light paths take the form, at least between the light source and the light path selector unit, of free radiation light paths which are not bound to a medium which defines the light path.

43. The illuminator according to claim 25, characterised in that the light output or the light outputs are formed on the basis of a respective light guide.

44. The illuminator according to claim 25, characterised in that the control unit controls the light conditioning arrangement or light conditioning arrangements.

* * * * *